United States Patent [19]

Lo

[11] Patent Number: 4,870,181
[45] Date of Patent: Sep. 26, 1989

[54] PROCESS FOR THE PREPARATION OF 2-ALKOXY-N-(1-AZABICYCLO[2.2.2])OCTAN-3-YL)AMINOBENZAMIDES

[75] Inventor: Young S. Lo, Richmond, Va.

[73] Assignee: A. H. Robins Company, Incorporated, Richmond, Va.

[21] Appl. No.: 697,943

[22] Filed: Feb. 4, 1985

[51] Int. Cl.⁴ ............................................. C07D 453/02
[52] U.S. Cl. ...................................................... 546/133
[58] Field of Search ........................................ 546/133

[56] References Cited

U.S. PATENT DOCUMENTS 3,859,443 1/1975 Mrozik ................................. 424/324
4,088,639 5/1978 Zappelli et al. ............... 260/112.5 R

FOREIGN PATENT DOCUMENTS 2529548 1/1984 France ................................. 546/133

OTHER PUBLICATIONS

Skoog et al., Anal. Chem., 3rd ed., pp. 156–157.

Primary Examiner—Mary C. Lee
Assistant Examiner—J. Richter

[57] ABSTRACT

A process for the preparation of 2-alkoxy-N-(1-azabicyclo[2.2.2]octan-3-yl)aminobenzamides, which are gastric pharmaceuticals in monogastric animals having the formula:

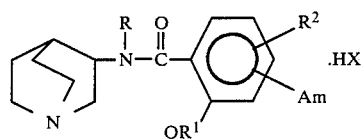

wherein R is hydrogen or loweralkyl,
R$^1$ is loweralkyl,
R$^2$ is hydrogen, halo or loweralkoxy,
Am is amino, methylamino or dimethylamino is disclosed wherein in the initial step an appropriate monoprotonated 3-aminoquinuclidine strong acid salt and an appropriate amino benzoic acid all in a 50–90 vol. % pyridine in water solution are reacted in the presence of N,N'-dialkylcarbodiimide. The free base may be obtained by conventional procedures from the mixtures with minimal purification effort.

10 Claims, No Drawings

PROCESS FOR THE PREPARATION OF 2-ALKOXY-N-(1-AZABICYCLO[2.2.2])OCTAN-3-YL)AMINOBENZAMIDES

BACKGROUND OF THE INVENTION

1. Field of Invention

The present invention relates to a novel process for the preparation of 2-alkoxy-N-(1-azabicyclo[2.2.2]octan-3-yl) aminobenzamides which have gastrokinetic and antiemetic pharmacologic properties. The process utilizes an N,N'-dialkylcarbodiimide condensation agent such as N,N'-dicyclohexylcarbodiimide (DCC) to react a strong mineral acid salt of 3-aminoquinuclidine or a loweralkyl substituted 3-aminoquinuclidine with an aminobenzoic acid derivative to form a benzamide in a medium comprised of 50 to 90 volume % pyridine and 50 to 10 volume % water wherein the equivalent ratio of strong acid to 3-aminoquinuclidinyl radical is 1:1 during reaction. The products of the invention always have a 2-methoxy radical and an amino radical on the benzene ring and may have other radicals on the benzene ring and are variously referred to herein as above or as quinuclidinyl subst-aminobenzamides.

2. Information Disclosure Statement

Preparation of amides from a carboxylic acid and an amine utilizing an N,N'-dialkylcarbodiimide as condensation agent in certain organic solvents is a known general procedure. However, the use of pyridine and water is not a general practice. Moreover, the benzoic acids of the present invention are also substituted by an amino group which must remain intact during the reaction and must not enter into the condensation reaction. The high solubility of 2-alkoxy-aminobenzoic acids in pyridine was not previously known.

The condensation reaction between the carboxylic acid group of an adenine derivative made functional by the amine group of a macromolecule also of adenine derivation utilizes a carbodiimide, including DCC, in water or in a mixture formed by water and water soluble organic solvent (e.g., pyridine, tetrahydrofuran, dioxane, etc.) at temperatures of 5° to 50° C., preferably at room temperature, has been disclosed in U.S. Pat. No. 4,088,639. In that disclosure the amount of pyridine exemplified in relation to water is less than and out of the range of the present invention and the reactants are of a macromolecular nature.

Preparation of N-(1-azabicyclo[2.2.2]octan-3-yl) benzamides substituted by an amino radical on the benzamide moiety in yields of 15–38% is disclosed in French Pat. No. 2,529,548. In that patent a yield of 15% of 4-amino-N-(1-azabicyclo[2.2.2]oct-3-yl)-5-chloro-2-methoxybenzamide maleate from reaction of 4-amino-5-chloro-2-methoxybenzoic acid, 3-aminoquinuclidine dihydrochloride and ethyl chloroformate in dimethylformamide and triethylamine followed by preparation of the salt was reported. The method of preparation disclosed does not employ an N,N'-dialkylcarbodiimide. In contrast, the present invention employs a monoprotonated strong acid salt of a 3-aminoquinuclidine in pyridine water solution.

In an application U.S. Ser. No. 597,275, filed on Apr. 6, 1984, 2-alkoxy-N-(1-azabicyclo[2.2.2]octan-3-yl) aminobenzamides were disclosed from reaction of such as 4-amino-5-chloro-2-methoxybenzoic acid and 3-aminoquinuclidine in tetrahydrofuran utilizing 1,1-carbonyldiimidazole as condensation agent. The method requires the free base of a 3-aminoquinuclidine which is difficult to obtain and the condensation agent is toxic and thus the method is impractical for large scale production.

SUMMARY AND OBJECTS OF THE INVENTION

The invention is especially concerned with economical procedures for preparing 2-alkoxy-N(1-azabicyclo[2.2.2]octan-3-yl)aminobenzamides in consistent high yield and high purity.

The 2-alkoxy-N-(1-azabicyclo[2.2.2]octan-3-yl)aminobenzamides preparable by the process of the present invention have the formula:

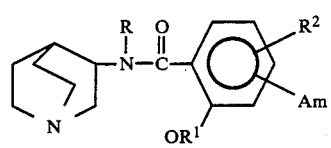

Formula I wherein R is hydrogen or loweralkyl; $R^1$ is loweralkyl; $R^2$ is selected from the group consisting of hydrogen, halo or loweralkoxy, and Am is selected from amino, methylamino or dimethylamino, and the strong mineral acid addition salts thereof. Strong mineral acids are exemplified by hydrochloric, hydrobromic, sulfuric, phosphoric or methane sulfonic acid and the like.

In the further definition of symbols in the formulas hereof and where they appear elsewhere throughout this specification and the claims, the terms have the following significance.

The term "loweralkyl" as used herein includes straight and branched chain radicals of up to eight carbons inclusive and is exemplified by such groups as methyl, ethyl, propyl, isopropyl, butyl, amyl, hexyl, heptyl, and octyl radicals and the like. The term "loweralkoxy" has the formula —O—loweralkyl.

The terms "halo" or "halogen" when referred to herein include fluorine, chlorine, bromine and iodine unless otherwise stated.

The term "N,N'-dialkylcarbodiimide" is intended to include any condensation agent suggestive of the generic term and will produce a by-product which is a water insoluble urea exemplified particularly by N,N-dicyclohexylcarbodiimide (DCC) and N,N'-diisopropylcarbodiimide.

The gastrokinetic pharmacological activity mentioned above was determined by the method of Droppleman, D., Gregory, R., and Alphin, R., J. Pharmacological Methods 4(3) 227–30 (1980) wherein the rate of emptying of a test meal in rats compared to controls was observed.

Anti-emetic properties are exhibited in the compounds when tested by the procedure of Chen and Enxor, J. Pharmac. Exp. Ther. 98, 245–250 (1950) and Leonard, A. et al., J. Pharmac. Exp. Ther. 154, 339–345 (1966).

Anti-emetic properties in the control of emesis due to administration of platinum anti-cancer drugs were determined by a modification of the method described by Gylys, J. A., in Res. Commun. Chem. Pathol, Pharmacol. 23, No. 1, January 1979, pp 61–68 as follows: cisplatin (cis-diamminedichloroplatinum) is administered at a dose of 3 mg/kg intravenously to non-fasted dogs (both sexes). Ninety minutes after cis-platinum administration, the test drug in saline at a dose volume of 2 ml/kg is administered intravenously. A control group of dogs are given the cisplatin followed by saline at 90 min, without test drug. The dogs are observed continuously for a period of 4 hr counting the number of emetic episodes compared to emetic eposides observed for the controls.

The process of the present invention is based on the discovery that 2-alkoxy-N-(1-azebicyclo[2.2.2]octan-3-yl) aminobenzamides can be prepared in very high yields in a reasonable time of about 24 hrs or less when an N,N'-dialkylcarbodiimide condensation agent is added to a pyridine-water solution of a 3-aminoquinuclidine mono-strong acid addition salt, i.e., the ratio of strong acid to quinuclidine nitrogen is about 1:1, and a 2-alkoxy-amino benzoic acid wherein during reaction, the ratio of pyridine to water may vary from about 50–50 volume % to about 90:10 volume %, all without uneconomical loss of the condensation agent.

In the search for an economical procedure for converting these relatively high cost reactants: the 3-aminoquinuclidines and the aminobenzoic acids, to the desired benzamides, it was found that the 2-alkoxy-aminobenzoic acids used to prepare compounds of Formula I have relatively high solubility in pyridine compared to other common solvents such as methylene chloride, acetonitrile and basic solvents such as triethylamine or N-methylmorpholine and that when such a pyridine solution is mixed with a water solution comprised of a 3-aminoquinuclidine mono-strong acid salt, and may contain a salt such as sodium chloride resulting from converting a di-strong acid salt of 3-aminoquinuclidine to a mono salt, a third and novel solution is formed having relatively high percentage of reactants which is advantageously prepared and used prior to addition of the condensation agent.

Data in Table 1 based on the examples hereinbelow demonstrate that superior yields of about 85–95% of theory are attainable in about 24 hr reaction time when the proton ratio to quinuclidine nitrogen, i.e., the ratio of strong acid to quinuclidine nitrogen, is about 1:1 as compared to a 2:1 ratio where yields were only 41–66% of theory. It may be further stated that the reaction does not go to completion in a reasonable length of time at a higher proton ratio than about 1:1 and that much more DCC is required if the reaction time is extended to complete the reaction. Other results have shown that when the proton quinuclidine nitrogen ratio is less than about 1:1, N,N'-dialkylcarbodiimides are rapidly destroyed.

Chemical equations illustrating reactions involved in the process are given in Chart I.

TABLE I

Effect of Proton:Quinuclidine Nitrogen Ratio on Yield

| Compound Example No. | Equiv. Ratio $H^+$:Quinuclidine-N | Molar Ratio DCC:3-amino-quinuclidine | Vol. % Ratio Pyridine: Water | Reaction Time Hr. | Yield, % Benzamides, % of Theory |
|---|---|---|---|---|---|
| 1 | 1:1 | 1.75:1 | 77.5:22.5 | 72 (a)* | 84 |
| 2 | 1:1 | 1.63:1 | 78.7:21.3 | 22 (a) | 94 |
| 3 | 1:1 | 2.6:1 | 50:50 | 84 (a)* | 89 |
| 4 | 1:1 | 1.45:1 | 88:22 | 24 (a) | 95 |
| 5 (comparative) | 2:1 | 1.8:1 | 81:19 | 21 (b) | 41.5 |
| 6 (comparative) | 2:1 | 2.1:1 | 85.15 | 24 (b) | 65.5 |

(a) No appreciable amount of 3-aminoquinuclidine left.
(b) Appreciable amount of 3-aminoquinuclidine remained.
*Includes time the reaction mixture was left in contact over the weekend for convenience but not of necessity for completion of reaction.

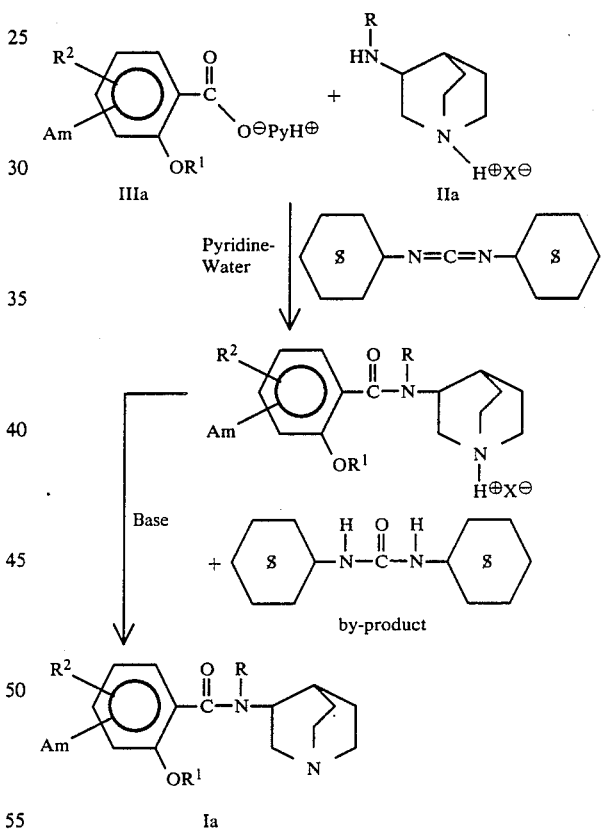

CHART I

It is therefore a primary object of the invention to provide a process for the efficient and economical conversion of 3-aminoquinuclidines and 2-alkoxy-aminobenzoic acids to 2-alkoxy-(1-azabicyclo[2.2.2]octan-3-yl)aminobenzamides which are highly effective antiemetic and gastric emptying agents in monogastric animals.

Another object is to provide pyridine-water solutions having relatively high concentrations of the 2-alkoxy-aminobenzoic acids and 3-aminoquinuclidines which are useful in preparing the 2-alkoxy-N-(1-azabicyclo[2.2.2]octan-3-yl) aminobenzamides.

Additional objects will become apparent to one skilled in the art and still others will become apparent hereinafter.

DETAILED DESCRIPTION OF THE INVENTION

A schematic of a detailed procedure illustrating the process for preparation of the free base of the 2-alkoxy-N-(1-azabicyclo[2.2.2]octan-3-yl]aminobenzamides, which process provides overall consistent yields of the order of 85–95% of theory based on the most expensive starting materials, the 3-aminoquinuclidine salts, is presented in Chart II. The condensation agent illustrated is DCC. The feasibility of the process depends on a combination of factors which include the use of a novel pyridine-water solution of high concentration of reactants and the use of a 3-aminoquinuclidine strong acid salt in its monoprotonated ratio.

In the flow diagram in Chart II the process operation is extended beyond the primary reaction step to show final isolation of the free base of the benzamide and it should be realized that the initial use of pyridine in the 50–90 vol % range to water and the proton to quinuclidine nitrogen ratio of about 1:1 influences not only the amount of dialkylcarbodiimide consumed, the speed of reaction, the productivity per unit volume, the yield from starting materials throughout the process, but also the purity and lessened need to separate unreacted starting materials throughout the process.

CHART II
Flow Diagram Illustrating Process

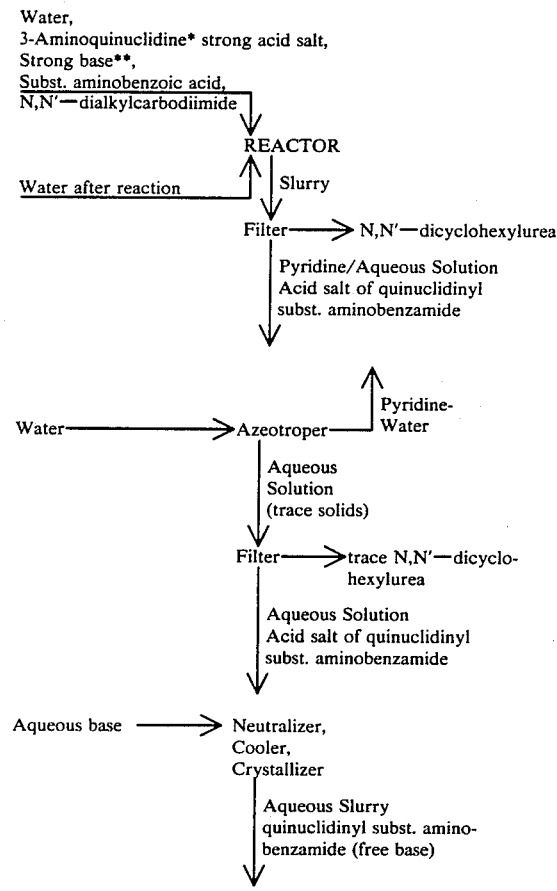

CHART II
Flow Diagram Illustrating Process

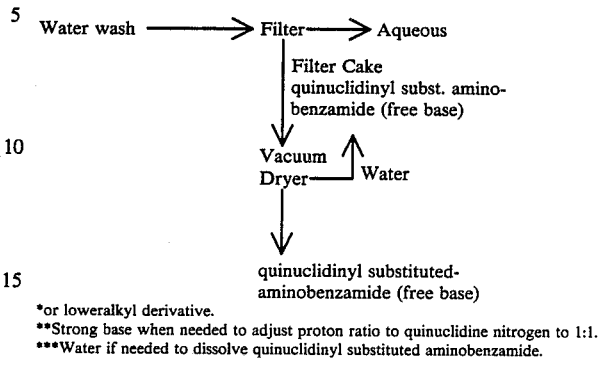

*or loweralkyl derivative.
**Strong base when needed to adjust proton ratio to quinuclidine nitrogen to 1:1.
***Water if needed to dissolve quinuclidinyl substituted aminobenzamide.

Prior to reaction; i.e., addition of condensation agent (e.g. DCC), a novel solution is preferably prepared comprised of pyridine, water and a 3-aminoquinuclidine mono-strong acid compound of the formula:

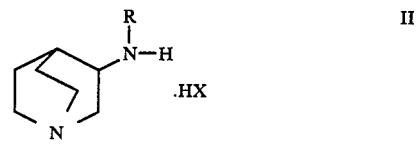

wherein R is hydrogen or loweralkyl, an aminobenzoic acid compound of the formula:

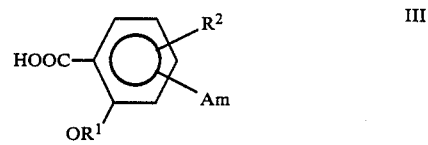

wherein $R^1$ is loweralkyl; $R^2$ is selected from the group consisting of hydrogen, halo or loweralkoxy, and Am is selected from amino, methylamino or dimethylamino and wherein the amount of said 3-aminoquinuclidine mono-strong acid salts ranges from about 5–15 wt. %, the amount of said aminobenzoic acid ranges from about 5–15 wt. % and the volume ratio of pyridine to the volume ratio of water ranges from 50:50 to 90:10. The novel solution is preferably prepared by adding a strong base, preferably aqueous alkali-metal base, to a water solution of a di-strong acid salt of a 3-aminoquinuclidine, preferably, for example, 3-aminoquinuclidine dihydrochloride, to form a solution of the 3-aminoquinuclidine mono-strong acid salt and mixing the aqueous solution with a pyridine solution of the aforesaid aminobenzoic acid to form a solution of both reactants.

Comprehensively stated, the overall process of the invention when extended beyond the initial reaction step to include work-up and final isolation of the free base, is comprised of reacting monoprotonated strong acid salt of a 3-aminoquinuclidine, Formula II above, preferably prepared by reacting a strong base with the dihydrochloride salt and a 2-alkoxy-aminobenzoic acid derivative, Formula III above, in a 50–90% vol. % pyridine to 50–10 vol. % water solution and using an N,N-dialkylcarbodiimide condensation agent, e.g., DCC, to give the 2-alkoxy-N-(1-azabicyclo[2.2.2]octan- 3-yl)aminobenzamide acid addition salt and adding water if necessary to dissolve said benzamide acid addition salt and filtering to remove by-product N,N'-dialkylurea to give a solution comprised of pyridine, water and an acid addition salt of said benzamide, azeotroping off the pyridine and isolating the acid salt or further purifying by neutralizing the acid salt with a strong base and isolating the free base of a 2-alkoxy-N-(1-azabicyclo[2.2.2]octan-3-yl)aminobenzamide by conventional means. If desired, the free base may be reconverted to the same acid addition salt or converted to another acid addition salt such as maleate, oxalate, fumarate, hydrobromide, etc.

The invention encompasses the following novel steps singly or in consecutive combination, i.e., (1) alone, (1) and (2) alone or 1, 2 and 3 and the novel solution of reactants prepared in step 1 prior to addition of condensation agent and described hereinabove.

Step 1, reacting a 3-aminoquinuclidine acid addition salt having the formula:

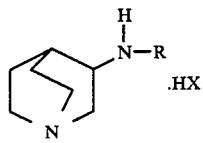

wherein R is hydrogen or loweralkyl and X is the anion of a strong mineral acid and the equivalent ratio of HX to quinuclidine nitrogen is about 1:1 with an aminobenzoic acid derivative having the formula:

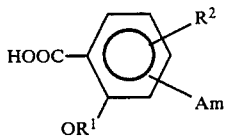

wherein R¹ is loweralkyl;
R² is selected from the group consisting of hydrogen, halo or loweralkoxy;
and Am is selected from amino, methylamino or dimethylamino
in the presence of the condensation agent, an N,N-dialkylcarbodiimide in a pyridine water solution wherein the volume % pyridine to volume % water ratio may range from 50:50 to 90:10 at a temperature of about 0°–50° C. to give a mixture comprised of pyridine, water, and an N-(1-azabicyclo[2.2.2]octan-3-yl aminobenzamide acid addition salt having the formula:

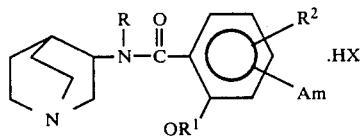

wherein R, R¹, R², Am, and X are as defined above and by-product N,N'-dialkylurea.

Step 2, diluting the mixture prepared in step 1, if necessary, with water to dissolve any precipitated said benzamide acid addition salt, separating by-product N,N'-dialkylurea to give a pyridine-water solution of said benzamide acid addition salt and removing pyridine, preferably at reduced pressure as a pyridine-water azeotrope, adding water, if necessary, during azeotroping and separating a small amount of N,N'-dialkylurea to give a water solution of said benzamide acid addition salt.

Step 3, adding a strong base to the water solution prepared in step 2 to neutralize the acid addition salt, cooling to enhance crystallization, filtering, washing, and drying the crystals to obtain the free base of said 2-alkoxy-N-(1-azabicyclo[2.2.2]octan-3-yl)aminobenzamide having the formula:

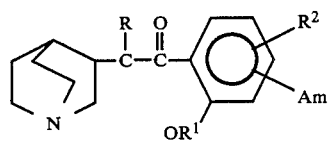

wherein R, R¹, R² and Am are as defined above, and which may have water associated therewith.

The following description is applicable to the foregoing process.

In step 1, the monoprotonated 3-aminoquinuclidine (or derivative thereof) strong acid addition salt in aqueous solution is most conveniently derived from a diprotonated strong mineral acid addition salt, preferably the dihydrochloride salt, by dissolving the diprotonated salt in water and adding about one equivalent of a strong base in an aqueous solution, preferably sodium hydroxide solution. The 2-methoxy-aminobenzoic acid derivative is preferably dissolved in the pyridine required for the reaction and the solution obtained is mixed together with the foregoing aqueous solution to obtain a third solution. The foregoing reactants, i.e., compounds of Formula II and Formula III, should be present in the range of 10–30 wt. % of the total solution at this point (molar equivalent weights are approximately equal so that each will be present in the range of about 5–15 wt. %) and the pyridine and water should be kept within a ratio range of 50–90 vol. % pyridine to 50–10 vol. % water, preferably about 75–85 vol. % pyridine to 15–25% water. N,N'-Dialkylcarbodiimide, e.g., DCC, is added to the solution and the reaction temperature is maintained at 0°–50° C., preferably about 25° C. for a period of time to effect conversion to the benzamide, usually about 10–24 hr or less being required. The amount of N,N'-dialkylcarbodiimide required is less at the higher pyridine to water ratio.

In step 2, dilution of the pyridine-water mixture prepared in step 1 with water accomplishes the following: dissolves any undissolved 2-alkoxy-N-(1-azabicyclo[2.2.2]octan-3-yl)aminobenzamide acid addition salt, hydrolyzes any unused condensing agent and aids in precipitation of by-product N,N'-dialkylurea, e.g., N,N'-dicyclohexylurea, preparatory to filtration to remove the bulk of the dialkylurea. The azeotroping step as stated above removes pyridine which results in further precipitation of dialkylurea and is done preferably at reduced pressure and temperature.

In step 3, the water solution prepared in step 2, containing the benzamide acid addition salt, is neutralized, cooled, and the crystals obtained are filtered off in a conventional manner, washing with water until pH of the filtrate is dropped to about 8–9. The crystals are then dried at temperatures from about 25°–100° C. at reduced pressure to give the degree of drying desired.

The following Examples 1–4, 7, 8 and preceding description and charts serve to illustrate the process of the invention; however, the scope of the invention is not limited thereto. Comparative Examples 5 and 6 form basis for comparison with procedure outside the scope of the present invention.

EXAMPLE 1

N-(1-Azabicyclo[2.2.2]octan-3-yl)-5-chloro-2-methoxy-4-(methylamino)benzamide, hydrochloride [1:1]

Preparation of Title Compound in Crude Mixture with Pyridine and Water

To an agitated mixture prepared by dissolving 1,180 g (5.9 mole) of 3-aminoquinuclidine dihydrochloride in 1.7 liters of water and adding 462 g (5.9 mole) of 51% aqueous, sodium hydroxide and 400 g of ice was added a solution containing 1352.4 g (6.3 mole) of 4-(N-methylamino)-5-chloro-2-methoxybenzoic acid in 8 liters of pyridine. The mixture was cooled to 21° C. and 1,440 g (7.0 mole) of DCC was added. Cooling was discontinued and the temperature rose to 28° C. after 1 hr and dropped to 25° C. after another 3 hr. Another 500 g (2.36 mole) of DCC was added and the mixture was allowed to stir overnight [TLC (15% ammonium hydroxide in methanol) indicated some 3-aminoquinuclidine was unreacted]. Concentrated hydrochloric acid (15 ml) was added and the mixture was stirred for ½ hr. Additional DCC, 200 g (1.0 mole) was added and the mixture was stirred for 48 hr. TLC indicated that the 3-aminoquinuclidine had all reacted (see Example 2 for TLC procedure).

Isolation of Free Base and Reconversion to the Monohydrochloride Salt

The mixture was diluted to a volume of 40 liters with water, stirred overnight and filtered to remove N,N'-dicyclohexylurea. The filter cake was rinsed with 3 liters of water. The reddish-brown filtrate amounting to 22 liters was concentrated to a volume of 10 liters. Water, 3 liters, and 200 g of activated charcoal were added and the mixture was stirred overnight and filtered to remove the charcoal. To the filtrate was added dropwise, 470 g (6.0 mole) of 51.1% aqueous sodium hydroxide (seeding with free base of the title compound part way through the addition) and heavy precipitate was obtained. The mixture was filtered and the filter cake was dried in a vacuum oven to give 1665 g of the free base of the title compound. The free base was dissolved in 6.7 liters of isopropyl alcohol and the solution was filtered. To the filtrate under agitation was added 428 ml of concentrated hydrochloric acid. The precipitate was collected and rinsed with 1.5 liters of isopropyl alcohol under suction filtration and nitrogen blanket and dried overnight at 75° C. under high vacuum. Yield of white powder, the hydrochloride salt, was 1784 g (84%).

Analysis: Calculated for $C_{16}H_{23}N_3O_2Cl_2$: C, 53.34; H, 6.44; N, 11.66 Found: C, 53.42; H, 6.57; N, 11.61

EXAMPLE 2

4-Amino-N-(1-azabicyclo[2.2.2]octan-3-yl)-5-chloro-2-methoxybenzamide monohydrochloride monohydrate Preparation of Title Hydrochloride in Pyridine-Water Mixture To a reactor having an agitator were added 11 liters of water, 7.30 kg (36.7 mole) of 3-aminoquinuclidine dihydrochloride and a solution made by mixing 2.93 kg (36.7 mole) of 50% sodium hydroxide and 2.44 kg of crushed ice to give a solution of 3-aminoquinuclidine monohydrochloride. To the cooled reactor solution (30° C.) was added a solution of 45 liters of pyridine and 8.12 kg (40.3 moles, i.e., an excess over the 3-aminoquinuclidine) of 4-amino-5-chloro-2-methoxybenzoic acid, an additional 10 liters of pyridine being used to rinse all the latter solution into the reactor. Cooling was stopped and the reaction mixture was stirred for ½ hr. To the reaction mixture was added 8.89 kg (43.0 moles) of warm melted DCC and the mixture was stirred at 25° C. for 6 hr. TLC of a sample, using 15% ammonium hydroxide in methanol on a silica gel plate by the method of P. Haefelfinzer in J. of Chromatography, 48 (184) 1970, showed the presence of unreacted 3-aminoquinuclidine. An additional 3.48 kg (16.8 mole) of DCC was added and the mixture was stirred for 16 hr. A repeat of the TLC test showed no 3-aminoquinuclidine was present.

Product Work-Up to Obtain Free Base

The reaction mixture was diluted with the addition of 46 liters of water. The mixture was stirred for several hours, then was vacuum filtered to remove the by-product N,N'-dicyclohexyl urea. The filtrate was vacuum distilled at 25 inches Hg to remove pyridine. When the pot temperature rose to 50° C., another 18 liters of water was added and the vacuum distillation was continued to a pot temperature of 65° C. The vacuum was released and 6 liters of water was added to the mixture to dissolve precipitated product hydrochloride salt. The mixture was filtered to remove a small amount of undissolved solids. The filtrate was cooled to 15° C. and 2.93 kg (36.6 moles) of 50% sodium hydroxide was added to precipitate free base of the title compound. The mixture was cooled further to 10° C. and filtered. The filter cake was washed with water until the pH of the filtrate had dropped to 8–9. The off-white solid was dried at 100° F. under 25 inches Hg vacuum for 16 hr to give 12.965 kg of free base hydrate containing 15% by weight of water.

Reconversion to Hydrochloride Salt

The free base hydrate was added to 50 liters of isopropyl alcohol and the mixture was warmed to 50° C. and filtered to remove a small amount of white insoluble sludge. An additional 15 liters of isopropyl alcohol was used in transfer and washing. The clarified filtrate was cooled to 15° C. and 2.96 liters of aqueous 37% hydrochloric acid solution was added slowly. The mixture was cooled for 26 hr and the white solid was collected by vacuum filtration. After drying to constant weight, 12.56 kg of title monohydrochloride monohydrate was obtained which represents a 94% overall yield (based on the limiting reactant 3-aminoquinuclidine hydrochloride), m.p. 154°–156° C.

Analysis: Calculated for $C_{15}H_{23}N_3O_3Cl_2$: C, 49.46; H, 6.36; N, 11.54 Found: C, 49.38; H, 6.44; N, 11.46

EXAMPLE 3

4-Amino-N-(1-azabicyclo[2.2.2]octan-3-yl]-5-chloro-2-methoxybenzamide

Preparation of Hydrochloride of Title Compound in Pyridine-Water Mixture

To a solution of 60 ml of pyridine containing 10.8 g (0.0535 mole) of 4-amino-5-chloro-2-methoxybenzoic acid was added an aqueous solution containing 3-aminoquinuclidine monohydrochloride prepared by adding 2 g (0.05 mole as 50% aqueous) sodium hydroxide to 60 ml of water and thereafter adding 10 g (0.05 mole) of 3-aminoquinuclidine dihydrochloride to the sodium hydroxide solution. To the resulting solution was added 12.4 g (0.0585 mole) of N,N'-dicyclohexylcarbodiimide. After stirring overnight at room temperature, unreacted 3-aminoquinuclidine was present and an additional 5.15 g (0.0243 mole) of DCC was added. After stirring another 8 hr at room temperature, an additional 10.3 g DCC was added and the mixture was stirred over the weekend (approx. 60 hr).

Isolation of Free Base

The reaction mixture was filtered to remove N,N'-dicyclohexyl urea by-product, the cake being washed with water into the filtrate. The filtrate showed (TLC, using the method described in Example 2) a small amount of unreacted 3-aminoquinuclidine was present. Pyridine was evaporated off, adding water as necessary. The aqueous residue was filtered to remove a trace of gummy solid. The filtrate was made basic and seeded. The precipitate was collected, rinsed 3 times with water, and dried at room temperature and 0.5 mm Hg vacuum for about 2 hr to give 14.6 g of product which was determined by NMR analysis to contain about 1 mole of water per mole of the benzamide. Yield based on the monohydrate composition was 89%.

EXAMPLE 4

4-Amino-N-(1-azabicyclo[2.2.2]octan-3-yl)-5-chloro-2-methoxybenzamide monohydrochloride, monohydrate

Preparation of Hydrochloride of Title Compound in Pyridine-Water Mixture

To a solution of 1.2 kg (6 mole) of 3-aminoquinuclidine dihydrochloride (99.5% pure) in 1.8 liters of water was added a solution of 240 g (6.0 mole) of sodium hydroxide in 630 ml of water. To the resulting solution (cooled in a water bath) was added a solution of 1.34 kg (6.5 mole) of 4-amino-5-chloro-2-methoxybenzoic acid (98% pure) in 8.0 liters of pyridine. An additional 1 liter of pyridine was used to rinse in the solution. The temperature rose to 28° C. and then was brought down to 20° C. with a water bath. To the mixture was added 1.47 kg (7.0 mole) of DCC) 98% pure) with cooling to about 15°-23° C. The reaction mixture was allowed to stir overnight and then another 500 g (2.4 mole) of DCC was added. The reaction mixture was stirred at about 25° C. for 5 hr, after which time only a minute amount of unreacted 3-amino-quinuclidine remained. The mixture was allowed to stir for 3½ hr longer and 3.0 liters of water was added. After stirring overnight, the mixture was filtered to remove N,N'-dicyclohexylurea on sintered glass (filter paper disintegrates). The filter cake was washed to the point of removing all trace of yellow color. The total volume of filtrate and rinsing combined was 21 liter. The volume was reduced, using a flash evaporator to 6.5 liter. The volume was further reduced under 26" mercury vacuum to 4.0 liters. To the concentrate was added 6 liters of n-propyl alcohol. After standing overnight the crystals were filtered off (with difficulty) and dissolved in a warm mixture of 4 liters of isopropyl alcohol and 300 ml of water. The turbid solution was filtered quickly to remove some insoluble impurity. The filtrate was cooled and diluted with 4 liters of isopropyl alcohol. The precipitate was collected by filtration. Second and third crops of crystals were obtained by concentrating the filtrate (mother liquor) each time.

Conversion to Free Base

The solids were combined and dissolved in the minimum amount of water and converted to the free base by adding sodium hydroxide. The free base was separated by filtration.

Reconversion to the Hydrochloride Salt

The free base was dissolved in isopropyl alcohol and the solution was treated with concentrated hydrochloric acid. On refrigeration, the hydrochloride salt precipitated. The salt was recrystallized from 5 ml/g of 90% isopropyl alcohol. Total yield of title product from all crops was 95% of theory.

COMPARATIVE EXAMPLE 5

N-(1-Azabicyclo[2.2.]oct-3-yl)-5-chloro-2-methoxy-4-methylamino)-benzamide hydrochloride [1:1]

To a stirred solution of 36 g (0.167 mole) of 4-methylamino-5-chloro-2-methoxybenzoic acid in 200 ml of pyridine was added an aqueous solution of 32 g (0.167 mole) of 3-aminoquinuclidine dihydrochloride in 60 ml of water to give a clear solution. The solution was cooled in a cold water bath and a solution of 41.30 g (0.201 mole) of DCC in 20 ml of pyridine was added dropwise over 30 min time. The mixture was stirred at room temperature for 5.5 hr and another portion of 27.5 g (0.134 mole) of DCC in 40 ml of pyridine was added. The mixture was stirred overnight at room temperature. The N,N'-dicyclohexyl urea by-product was removed by filtration and washed with about 600 ml of water. The filtrate was evaporated to dryness and the residue was heated with water. The mixture was filtered and the insoluble material was rinsed with hot water. The filtrate was acidified to pH 2–3 with concentrated hydrochloric acid and extracted twice with 200 ml of methylene chloride each time. The aqueous solution was adjusted to pH 10–12 with 50% aqueous sodium hydroxide and the solution was extracted twice with 250 ml of methylene chloride each time. The combined extract was washed with 200 ml of saturated sodium chloride, dried over magnesium sulfate, treated with activated charcoal and filtered. To the filtrate was added 150 ml of isopropyl alcohol and the solution was evaporated to give 51 g of an oil. The oil was dissolved in 150 ml of hot isopropyl alcohol and treated with concentrated hydrochloric acid to form a slurry. The mixture was stirred at room temperature for 2 hr. and then 300 ml of dry acetone was added. After further stirring. the solid was collected, washed twice with dry acetone and dried under a stream of nitrogen to give 34.8 g dried solid. The solid was recrystallized from methanol-ethanol-water to give 24.84 g (41.5% of theory) of white solid product, m.p. 255°–258° C.

Analysis: Calculated for $C_{16}H_{23}N_3O_3Cl_2$: C, 53.34; H, 6.44; N, 11.66 Found: C, 53.04; H, 6.44; N, 11.61

COMPARATIVE EXAMPLE 6

(Ratio of 3-Aminoquinuclidin: HCl=1:2; pyridine:water 85-15).

4-Amino-N-(1-azabicyclo[2.2.2]octan-3-yl)-5-chloro-2-methoxybenzamide hydrochloride hydrate [1:1:1]

To a solution of 11 g (0.0546 mole) of 4-amino-5-chloro-2-methoxybendzoic acid and 8.5 g (0.0425 mole) of 3-aminoquinuclidine hydrochloride in 90 ml of pyridine and 20 ml of water was added 13 g (0.063 mole) of DCC using 10 ml of pyridine to rinse it in. The mixture became warm as solid N,N'-dicyclohexylurea began to deposit out. An additional 20 ml pyridine was added to facilitate stirring. TLC (see Example 2 for procedure) showed much 3-aminoquinuclidine starting material. Seven g (0.034 mole) of additional DCC and 10 ml of pyridine were added to the reaction mixture. The mixture was stirred overnight at room temperature and still contained unreacted 3-aminoquinuclidine. The reaction mixture was filtered to remove N,N'-dicyclohexylurea, (the filter cake being washed with water). The filtrate (and wash) was combined and concentrated to an oil which solidified on cooling. The N,N'-dicyclohexylurea cake was rinsed a third time and the rinse waer was used to dissolve most of the solidified oil and the mixture was filtered to remove unreacted 4-amino-5-chloro-2-methoxybenzoic acid. The filtrate was acidified with a few drops of conc. hydrochloric acid and then extracted twice with methylene chloride to remove more urea and the methylene chloride discarded. Additional methylene chloride and 50% aqueous sodium hydroxide were added to the cold aqueous layer until it became strongly basic. The layers were separated and the aqueous layer was extracted once more with methylene chloride. The methylene chloride layers were combined, washed with sodium chloride solution, dried, treated with activated charcoal, and filtered. The filtrate was evaporated and the foamy residue was dissolved in isopropyl alcohol. The solution was cooled and acidified with conc. hydrochloric acid (37%) Acetone was added to precipitate additional solid. The slurry was filtered and the cake was washed twice with acetone and dried to give 10.14 g (65.8%) of the title monohydrochloride monohydrate salt.

EXAMPLES 7a–d

Following the procedure of Example 2, but substituting the following for 4-amino-5-chloro-2-methoxybenzoic acid:
4-amino-5-bromo-2-methoxybenzoic acid,
4-amino-2,5-dimethoxybenzoic acid,
4-amino-2-methoxybenzoic acid, and
5-chloro-4-(dimethylamino)-2-methoxybenzoic acid,
there are obtained:
(a) 4-amino-N-(1-azabicyclo[2.2.2]octan-3-yl)-5-bromo-2-methoxybenzamide hydrochloride,
(b) 4-amino-N-(1-azabicyclo[2.2.2]octan-3-yl)-2,5-dimethoxybenzamide hydrochloride,
(c) 4-amino-N-(1-azabicyclo[2.2.2]octan-3-yl)-2-methoxybenzamide hydrochloride, and
(d) N-(1-azabicyclo[2.2.2]octan-3-yl)-5-chloro-4-(dimethylamino)-2-methoxybenzamide hydrochloride.

EXAMPLES 8a–b

Following the procedure of Example 2, but substituting the following for 3-aminoquinuclidine monohydrochloride:
3-(methylamino)quinuclidine monohydrochloride,
3-(ethylamino)quinuclidine monohydrochloride,
there are obtained:
(a) 4-amino-N-(1-azabicyclo[2.2.2]octan-3-yl)-N-methyl-5-chloro-2-methoxybenzamide monohydrochloride, and
(b) 4-amino-N-(1-azabicyclo[2.2.2]octan-3-yl)-N-ethyl-5-chloro-2-mehoxybenzamide monohydrochloride.

What is claimed is:

1. A process which comprises reacting a 3-aminoquinuclidine acid addition salt having the formula:

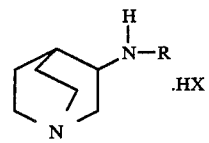

wherein R is hydrogen or loweralkyl, and X is the anion of a strong mineral acid and the equivalent ratio of HX to quinuclidine nitrogen is about 1:1 with an aminobenzoic acid derivative having the formula

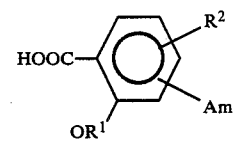

wherein $R^1$ is loweralkyl;
$R^2$ is selected from the group consisting of hydrogen, halo or loweralkoxy; and
Am is selected from amino, methylamino or dimethylamino,
in the presence of the condensation agent an N,N'-dialkylcarbodiimide in a pyridine water solution wherein the volume of pyridine to volume % water ratio ranges from 50:50 to 90:10 at a temperature of about 0°–50° C. to give a mixture comprised of pyridine, water, an N-(1-azabicyclo[2.2.2]octan-3-yl aminobenzamide acid addition salt having the formula

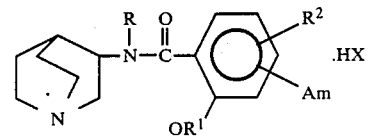

wherein R, $R^1$, $R^2$, Am and X are as defined above and by-product N,N'-dialkylurea.

2. A process of claim 1 wherein the 3-aminoquinuclidine acid addition salt is 3-aminoquinuclidine monohydrochloride.

3. A process of claim 1 wherein the aminobenzoic acid derivative is 4-amino-5-chloro-2-methoxy benzoic acid.

4. A process of claim 1 wherein the 3-aminoquinuclidine acid addition salt is 3-aminoquinuclidine monohydrochloride and the aminobenzoic acid derivative is 4-amino-5-chloro-2-methoxybenzoic acid and the benzamide produced is 4-amino-N-(1-azabicyclo[2.2.2]octan-3-yl)-5-chloro-2-methoxybenzamide monohydrochloride.

5. The process of claim 1 wherein the 3-aminoquinuclidine acid addition salt is 3-aminoquinuclidine monohydrochloride and the aminobenzoic acid derivative is 4-(N-methylamino)-5-chloro-2-methoxybenzoic acid and the banzamide produced is N-(1-azabicyclo[2.2.2]octan-3-yl)-5-chloro-2-methoxy-4-(methylamino)-benzamide monohydrochloride.

6. The process of claim 1 wherein the N,N'-dialkylcarbodiimide is N,N'-dicyclohexylcarbodiimide and the N,N'-dialkylurea is N,N'-dicyclohexylurea.

7. The process of claim 1 wherein the volume % ratio of pyridine to water ranges from 75:25 to 85:15.

8. A process which comprises the steps of:

Step 1, reacting a 3-aminoquinuclidine acid addition salt having the formula:

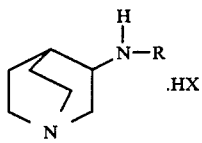

wherein R is hydrogen or loweralkyl and X is the anion of a strong mineral acid, and the equivalent ratio of HX to quinuclidine nitrogen is about 1:1 with an aminobenzoic acid derivative having the formula:

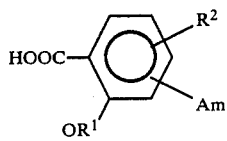

wherein R¹ is loweralkyl;
R² is selected from the group consisting of hydrogen, halo or loweralkoxy; and
Am is selected from amino, methylamino or dimethylamino in the presence of the condensation agent an N,N'-dialkylcarbodiimide in a pyridine water solution wherein the volume % pyridine to volume % water ratio may range from 50:50 to 90:10 at a temperature of about 0°-50° C. to give a mixture comprised of pyridine, water, an N-(1-azabicyclo[2.2.2]octan-3-yl-aminobenzamide acid addition salt having the formula:

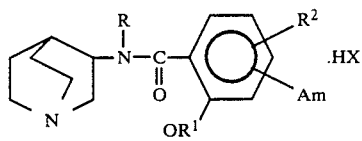

wherein R, R¹, R², Am and X are defined above and by-product N,N'-dialkylurea;

Step 2, diluting the mixture prepared in Step 1, if necessary, with water to dissolve any precipitated said benzamide acid addition salt, separating by-product N,N'-dialkylurea to give a pyridine-water solution of said benzamide acid addition salt and removing pyridine at reduced pressure as a water pyridine azatrope adding water, if necessary, and separating a small amount of N,N'-dialkylurea to give a water solution of said benzamide acid addition salt;

Step 3, adding a strong base to the water solution prepared in Step 2 to neutralize the acid component of the acid addition salt, cooling and crystallizing, filtering, washing, and drying the crystals to obtain the free base of said 2-alkoxy-N-(1-azabicyclo[2.2.2]octan-3-yl)-aminobenzamide having the formula:

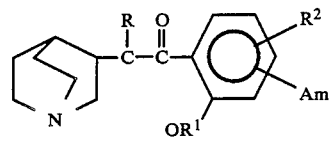

wherein R, R¹, R² and Am are as defined above.

9. A process for the preparation of an N-(1-azabicyclo[2.2.2]octan-3-yl)aminobenzamide and addition salt having the formula:

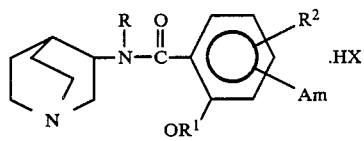

wherein R is hydrogen or loweralkyl;
R¹ is loweralkyl;
R² is selected from the group consisting of hydrogen, halo or loweralkoxy;
Am is selected from amino, methylamino or dimethylamino, and
X is the anion of a strong mineral acid in a pyridine-water solution which comprises mixing a first solution which is an aqueous solution comprised of a 3-aminoquinuclidine acid addition salt having the formula:

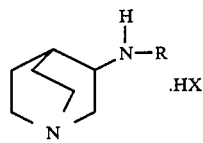

wherein R and X are as defined above, and the equivalent ratio of H⁺ to quinuclidine nitrogen is about 1:1 with a second solution, a pyridine solution having dissolved therein an amino benzoic acid derivative having the formula:

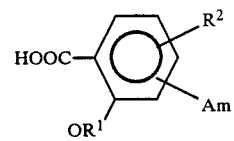

wherein R¹, R², and Am are as defined above to give a third solution having a volume % pyridine to water ratio ranging from 50:50 to 90:10 and adding thereto the condensation agent: N,N'-dialkylcarbodiimide in an amount sufficient to bring about conversion of substantially all the said quinuclidine salt to the said benzamide acid addition salt at about 0°-50° C. over a period of time, and thereafter filtering to remove by-product N,N'-dialkylurea to give a pyridine-water solution of said N-(1-azabicyclo[2.2.2]octan-3-yl)aminobenzamide acid addition salt.

10. A solution comprised of pyridine, water, a 3-aminoquinuclidine mono-strong acid salt of the formula:

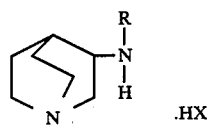

wherein R is hydrogen or loweralkyl, and the ratio of strong acid to quinuclidine nitrogen is about 1:1, an aminobenzoid acid compound of the formula:

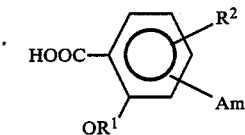

wherein $R^1$ is loweralkyl, $R^2$ is selected from the group consisting of hydrogen, halo or loweralkoxy, and Am is selected from amino, methylamino or dimethylamino and wherein the amount of said 3-aminoquinuclidine mono-strong acid salt ranges from about 5–15 wt. %, the amount of said aminobenzoic acid ranges from about 5–15 wt. % and the volume % ratio of pyridine to volume % water ranges from 50:50 to 90:10.

* * * * *